United States Patent [19]
Sasatani et al.

[11] Patent Number: 5,876,760
[45] Date of Patent: Mar. 2, 1999

[54] GRANULES CONTAINING PRANLUKAST, PROCESS FOR PRODUCING THE GRANULES, AND METHOD OF IMPROVING ADHESIVENESS OF PRANLUKAST

[75] Inventors: Seiei Sasatani; Masashi Shiota; Yoshinori Ii, all of Osaka, Japan

[73] Assignee: Ono Pharmaceutical Co., Ltd., Osaka, Japan

[21] Appl. No.: 981,083

[22] PCT Filed: Jun. 11, 1996

[86] PCT No.: PCT/JP96/01578

§ 371 Date: Dec. 12, 1997

§ 102(e) Date: Dec. 12, 1997

[87] PCT Pub. No.: WO96/41628

PCT Pub. Date: Dec. 27, 1996

[30] Foreign Application Priority Data

Jun. 12, 1995 [JP] Japan ................................. 7-169292

[51] Int. Cl.$^6$ ........................................................ A61K 9/16
[52] U.S. Cl. ............................................ 424/494; 514/453
[58] Field of Search ............................. 424/494; 514/453

[56] References Cited

FOREIGN PATENT DOCUMENTS 0 641 569 A1  3/1995  European Pat. Off. .
7-76516  3/1995  Japan .

OTHER PUBLICATIONS

International Search Report.
Akinobu Otsuka, Shinichi Hayashi "Pharmaceutics Centering around Powder" (Hirokawa Shoten), (25, 03, 76) pp. 146–155.
Funtai Kogakukai Seizai to Ryushi Sekkeibukai (ed.), *Particulate Design and Pharmaceutical Technique,* pp. 21–26, Yakugyo Jiho Co., Ltd. (Oct. 30, 1993).

*Primary Examiner*—Jose' G. Dees
*Assistant Examiner*—Michael A. Williamson
*Attorney, Agent, or Firm*—Sughrue, Mion, Zinn, Macpeak & Seas, PLLC

[57] ABSTRACT

Spray-dried granules comprising pranlukast (A) and one or more saccharide(s) (B) as essential ingredients and further comprising one or more water-soluble polymer(s) (C) and/or one or more surfactant(s) (D); a process for producing the same; and a method for improving adhesiveness of pranlukast are provided. According to the present invention, the very strong adhesiveness of pranlukast is reduced, and pranlukast-containing granules having little adhesiveness, a narrow particle size distribution, and good flow properties can be produced efficiently. The pranlukast-containing granules of the present invention cause no troubles in continuous production of capsules, tablets, and the like, and the resulting pranlukast-containing granules exhibit excellent disintegrating and dispersing properties.

19 Claims, No Drawings

GRANULES CONTAINING PRANLUKAST, PROCESS FOR PRODUCING THE GRANULES, AND METHOD OF IMPROVING ADHESIVENESS OF PRANLUKAST

TECHNICAL FIELD

This invention relates to spray-dried granules of pranlukast having improved adhesiveness which are useful for preparing pranlukast-containing tablets or capsules; a process for producing the same; and a method for improving adhesiveness of pranlukast.

BACKGROUND ART

4-Oxo-8-[(4-phenylbutoxy)benzoylamino]-2-(tetrazol-5-yl)-4H-1-benzopyran.½ hydrate (common name: pranlukast, hereinafter referred to as "pranlukast" in the specification including the claims) represented by formula:

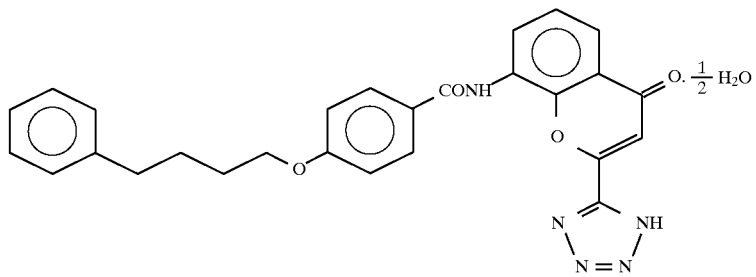

is a compound having a potential antagonistic action against leucotriene $C_4$ ($LTC_4$) and leucotriene $D_4$ ($LTD_4$) and is expected as a treating agent for allergic bronchial or pulmonary diseases, allergic shock, and various allergic inflammatory diseases.

However, pranlukast is fine powder having very strong adhesiveness. When pranlukast merely mixed with additives is formed into such dose forms as tablets or capsules, the pranlukast powder adheres to a punch, a die, a rotary table and the like, making continuous production difficult.

Improvement on physical properties of strongly adhesive fine powder is generally achieved by increasing the particle size of the raw material powder by agitation granulation, wet screening granulation, fluidized bed granulation, and the like. However, since the properties of powder containing pranlukast that is strongly adhesive fine powder in a high concentration depends on mainly the pranlukast present in a high concentration, an increase in particle size does not lead to improvement in powder properties, and continuous tabletting or capsule-filling is still impossible.

It is known that adhering to machinery can be prevented by (1) a method comprising adding a large quantity of an additive having little adhesiveness and granulating the mixture or (2) a method comprising coating strongly adhesive powder with lactose.

Pranlukast preparations prepared by method (1) are to have an increased size and are not deemed favorable to patients suffering from asthma and the like to whom pranlukast is applied. In fact, if the pranlukast content is reduced to about 10%, granules prepared in a conventional method can be continuously tableted or capsule-filled but only to produce large-sized preparations.

Method (2) is usually carried out by fluidized bed coating. However, the pranlukast powder gets coarse and gains a considerable size during fluidized bed coating, which necessitates a size regulating step. During the size regulating step, the coarse particles are destroyed to expose the drug with adhesiveness, eventually failing to improve the adhesiveness of the granules.

Accordingly, an object of the present invention is to provide pranlukast-containing granules having a narrow particle size distribution and good flow properties by modifying the strongly adhesive surface of pranlukast and to provide a method for producing the same.

Another object of the present invention is to provide pranlukast-containing granules which exhibit satisfactory disintegrating and dispersing properties after administration.

DISCLOSURE OF THE INVENTION

In order to accomplish the above objects, the inventors of the present invention have conducted extensive study. As a result, it has now been found that the surface of strongly adhesive pranlukast can be improved by granulating a pranlukast composition containing a relatively small amount of specific components by spray-drying to easily and efficiently provide granules having a high pranlukast content (concentration) which have a narrow particle size distribution and very good flow properties with little surface adhesiveness and that the resulting granules can be tableted or capsule-filled in a continuous production with no problem and also the resulting pranlukast preparations exhibit very satisfactory disintegration and dispersion after administration. The present invention has thus been completed based on these findings.

That is, the present invention provides:

1) Spray-dried granules comprising pranlukast (A) and one or more saccharide(s) (B) as essential ingredients, and further comprising one or more water-soluble polymer(s) (C) and/or one or more surfactant(s) (D);
2) The spray-dried granules according to (1), which comprise one or more saccharide(s) (B) and one or more water-soluble polymer(s) (C);
3) The spray-dried granules according to (1), which comprise one or more saccharide(s) (B) and one or more surfactant(s) (D);
4) The spray-dried granules according to (1), which comprise one or more saccharide(s) (B), one or more water-soluble polymer(s) (C), and one or more surfactant(s) (D);
5) The spray-dried granules according to any one of (1) to (4), wherein the saccharide is lactose or mannitol;
6) The spray-dried granules according to (1), (2) or (4), wherein the water-soluble polymer (C) is a cellulose compound or a synthetic polymer;
7) The spray-dried granules according to (6), wherein the water-soluble polymer (C) is hydroxypropyl cellulose, polyvinylpyrrolidone or polyethylene glycol;
8) The spray-dried granules according to (1), (3) or (4), wherein the surfactant (D) is polysorbate;

9) The spray-dried granules according to any one of (1) to (8), which comprise pranlukast (A); lactose and/or mannitol (B1); hydroxypropyl cellulose, polyvinylpyrrolidone, polyethylene glycol (C1) and/or polysorbate;

10) The spray-dried granules according to (9), which comprise pranlukast (A), lactose (B2), and hydroxypropyl cellulose (C2);

11) The spray-dried granules according to (9), which comprise pranlukast (A), lactose (B2), and polyethylene glycol (C3);

12) A process for producing spray-dried granules comprising spray-drying a suspension comprising pranlukast (A) and one or more saccharide(s) (B) as essential ingredients and further comprising one or more water-soluble polymer(s) (C) and/or one or more surfactant(s) (D); and 13) A method for improving adhesiveness of pranlukast comprising spray-drying into granules a suspension comprising pranlukast (A) and one or more saccharide(s) (B) as essential ingredients and further comprising one or more water-soluble polymer(s) (C) and/or one or more surfactant (s) (D).

The present invention will be described in more detail.

As stated above, pranlukast is fine powder with very strong adhesiveness. If a combination of pranlukast and additives is granulated by agitation granulation, wet screening granulation or fluidized bed granulation, as is a common practice with other strongly adhesive substances, to obtain granules having pranlukast in high concentrations, the resulting granules cause troubles in continuous tableting or capsule-filling. Use of large quantities of additives having no adhesiveness makes the preparations unfavorably larger.

The inventors have investigated a spray-drying method aiming at production of particles which contain pranlukast in high concentrations and yet have improved surface adhesiveness. As a result, they have succeeded in modifying the surface adhesiveness of pranlukast and obtaining granules containing pranlukast in high concentrations and having a narrow particle size distribution and very good flow properties by spray-drying a suspension of pranlukast (component (A)) together with a water-soluble polymer (component (C)) or a surfactant (component (D)) which improves wettability and dispersibility of pranlukast and a saccharide (component (B)) which can coat the surface of pranlukast particles.

The present invention is the first to realize an attempt to modify the surface of a strongly adhesive drug (pranlukast) to improve the adhesiveness by spray-drying the drug together with saccharides.

That is, spray-drying granulation is well known as described, e.g., in Nihon Funtai Kogyo Gijutsu Kyokai (ed.), *Granulation Handbook,* pp. 249–282, Ohm Sha (Mar. 10, 1991) and Funtai Kogakukai Seizai to Ryushi Sekkeibukai (ed.), *Particulate Design and Pharmaceutical Technique,* pp. 21–26, Yakugyo Jiho Co., Ltd. (Oct. 30, 1993).

Spray-drying has been adopted for the purpose of (a) improving solubility, (b) making slow-releasing preparations, (c) stabilizing drugs, and (d) powdering oily substances.

DETAILED DESCRIPTION OF THE INVENTION

According to the above-cited literature, applications of spray-drying to pharmaceutical preparations include:
1) Spray-dried solid dispersions comprising a water-soluble polymer matrix, such as polyvinylpyrrolidone or polyethylene glycol, having a drug uniformly dispersed therein;
2) Spray-dried preparations containing vitamin E acetate, which are obtained by emulsifying vitamin E acetate with a surfactant and finely powdering the emulsion by spray-drying along with colloidal silica; and
3) Surface modification of hydrophobic drugs to improve wettability with water, which comprises spray-drying the drug together with a surfactant.
4) Spray-drying is also applicable to fine powder of saccharides. In this case, a saccharide is spray-dried to obtain spherical granules having an increased particle size and improved flow properties.
5) In addition, JP-A-7-76516 (unexamined published Japanese patent application) discloses application of spray-drying to sparingly soluble drugs (e.g., phenytoin, sulfisoxazole, aminopyrine, secobarbital, prednisolone, nifedipine, griseofulvin, phenacetin, phenobarbital, amide compounds such as tolbutamide) for the purpose of improving the solubility, in which the drug is mixed with a hydrophilic vehicle (e.g., starch, cellulose, silicic anhydride) as an essential component and, if desired, a water-soluble vehicle (e.g., lactose, sucrose, mannitol), a binder (e.g., polyvinylpyrrolidone, polyvinyl alcohol, gelatin, sodium carboxymethyl cellulose, hydroxypropylmethyl cellulose, hydroxypropyl cellulose, dextrin), and a surfactant, and the mixture is spray-dried.

The differences of the present invention from applications (1) to (5) described above reside in the following points.

In application (1), a drug is dispersed on a molecular level in a water-soluble polymer matrix; on the other hand, in the present invention the drug exists in the state of solid crystals coated with a saccharide. Application (1) aims at improvement on a drug in solubility, while the object of the present invention is to improve adhesiveness of a drug.

In application (2), a drug exists in interstices among colloidal silica particles or is enclosed inside the colloidal silica particles, while the drug of the present invention exists as coated with a saccharide. Application (2) has its object in powdering an oily substance; on the other hand, the present invention proposes improvement of the surface properties of solid powder.

In application (3), a surfactant is used for the purpose of improving wettability of drug particles thereby to accelerate dissolution of the drug. In the present invention, the surfactant is used for improving wettability and dispersibility of the drug in preparing a suspension to be spray-dried thereby to achieve complete coating of the drug particles with saccharides, such as lactose. The effect obtained by the surfactant is acceleration of dissolution in application (3) but reduction in adhesiveness in the present invention.

Spray-drying of a saccharide alone according to application (4) aims to improve flow properties of the saccharide itself. It has turned out, however, that spray-drying of a suspension of pranlukast alone brings about no reduction of adhesiveness.

The effect of the granules exerted in application (5) consists in improvement of solubility of the drug; on the other hand, the effect of the present invention is reduction of adhesiveness.

Although it is known that spray-drying generally provide larger particle sizes with improved flow properties, applications to pharmaceuticals heretofore reported in the literature have been directed to improvement in solubility, powdering of oily substances, and improvement of dissolving properties, no report referring to an attempt to improve adhesiveness by adopting spray-drying. Therefore, a concrete method for accomplishing the object of the present invention is not found in the literature. Under the present situation, it is not easily anticipated from the prior art what kinds of assisting agents or additives pranlukast should be combined with when spray-dried to achieve reduction reduction in adhesiveness. The present invention succeeded for the first time in improving the adhesiveness of pranlukast by spray-drying a suspension of pranlukast, a saccharide, and a water-soluble polymer or a surfactant.

The present invention relates to spray-dried granules comprising pranlukast (A) and one or more saccharide(s) (B) as essential ingredients and further comprising one or more water-soluble polymer(s) (C) and/or one or more surfactant(s) (D), a process for producing the same, and a method for improving adhesiveness of pranlukast.

The pranlukast-containing granules according to the present invention can be obtained by suspending pranlukast (A) and one or more saccharide(s) (B) as essential ingredients and one or more water-soluble polymer(s) (C) and/or one or more surfactant(s) (D) in an appropriate solvent (e.g., water or a mixed solvent of water and an organic solvent, such as an alcohol) and spray-drying the suspension.

The pranlukast concentration in the spray-dried granules (granules to powder), while subject to variation according to the final use, generally ranges from 30 to 90% by weight, preferably 50 to 75% by weight. The particle size of the resulting spray-dried pranlukast granules can be adjusted in a range of from 20 to 1000 μm by controlling spray-drying conditions.

If desired, the pH of the suspension for spray-drying can be adjusted by addition of a pH adjusting agent, i.e., a base or an acid.

The saccharide as component (B) includes lactose, mannitol, sucrose, dextrin, dextran, trehalose, pullulan, and maltose, with lactose and mannitol being preferred. These saccharides can be used either individually or as mixture of two or more thereof.

For example, the saccharide is used in an amount of 10 to 100 parts by weight, preferably 30 to 60 parts by weight, based on 100 parts by weight of pranlukast.

The water-soluble polymer as component (C) includes cellulose compounds, such as hydroxypropyl cellulose, hydroxypropylmethyl cellulose, and methyl cellulose; and synthetic polymers, such as polyethylene glycol, polyvinylpyrrolidone, and polyvinyl alcohol; and gelatin. Cellulose compounds and synthetic polymers are preferably used. Hydroxypropyl cellulose, polyvinylpyrrolidone, and polyethylene glycol are still preferred. These water-soluble polymers can be used either individually or as a mixture of two or more thereof.

The water-soluble polymer is used in an amount of, for example, 1 to 30 parts by weight, preferably 5 to 20 parts by weight, based on 100 parts by weight of pranlukast.

The surfactant as component (D) includes polyoxyethylene hydrogenated castor oil, sorbitan monostearate, polysorbate, and alkylsulfuric esters, with polysorbate being preferred. These surfactants can be used either individually or as a mixture of two or more thereof. The surfactant is used in an amount of, for example, 0.5 to 2.5 parts by weight, preferably 0.5 to 1 part by weight, based on 100 parts by weight of pranlukast.

The base which may be added to the suspension includes ammonium carbonate, sodium hydroxide, potassium hydroxide, and a sodium hydrogenphosphate buffer. Weak bases such as ammonium carbonate are preferred. The acid includes citric acid, hydrochloric acid, and tartaric acid, with citric acid being preferred.

BEST MODE FOR CARRYING OUT THE INVENTION

The present invention will now be illustrated in greater detail with reference to Examples, Comparative Examples, and Test Examples, but it should be understood that the present invention is not construed as being limited thereto.

EXAMPLE 1

In 10 kg of purified water was dissolved 1 kg of hydroxypropyl cellulose, and 5 kg of lactose and 10 kg of pranlukast were added thereto to prepare a suspension. The suspension was spray-dried with a spray-drier under the following conditions to obtain 15.2 kg of spray-dried pranlukast granules. The resulting granules had an average particle size of about 100 μm.

Spray-drying Conditions:
Disk rotational speed: 8000 rpm
Air temperature at the inlet: 180° C.
Air temperature at the outlet: 100° C.
Suspension feed rate: 100 g/min

EXAMPLE 2

In 1.2 kg of purified water was dissolved 10 g of Polysorbate 80, and 400 g of mannitol and 1 kg of pranlukast were added thereto to prepare a suspension. The suspension was spray-dried with a spray-drier under the following conditions to obtain 1.35 kg of spray-dried pranlukast granules. The resulting granules had an average particle size of about 50 μm.

Spray-drying Conditions:
Disk rotational speed: 18000 rpm
Air temperature at the inlet: 200° C.
Air temperature at the outlet: 100° C.
Suspension feed rate: 30 g/min

EXAMPLE 3

In 180 kg of purified water was dissolved 10 kg of polyvinylpyrrolidone, and 40 kg of lactose and 100 kg of pranlukast were added thereto to prepare a suspension. The suspension was spray-dried with a spray-drier under the following conditions to obtain 145 kg of spray-dried pranlukast granules. The resulting granules had an average particle size of about 120 μm.

Spray-drying Conditions:
Disk rotational speed: 7000 rpm
Air temperature at the inlet: 180° C.
Air temperature at the outlet: 100° C.
Suspension feed rate: 1 kg/min

EXAMPLE 4

In 10 kg of purified water was dissolved 1 kg of polyethylene glycol, and 5 kg of lactose and 10 kg of pranlukast were added thereto to prepare a suspension. The suspension was spray-dried with a spray-drier under the following conditions to obtain 15.2 kg of spray-dried pranlukast granules. The resulting granules had an average particle size of about 100 μm.

Spray-drying Conditions:
Disk rotational speed: 8000 rpm
Air temperature at the inlet: 180° C.
Air temperature at the outlet: 100° C.
Suspension feed rate: 100 g/min

EXAMPLE 5

In 90 kg of purified water were dissolved 4 kg of polyethylene glycol and 1.9 g of ammonium carbonate, and 18.7 kg of lactose and 40 kg of pranlukast were added thereto to prepare a suspension. The suspension was spray-dried with a spray-drier under the following conditions to obtain 59.7 kg of spray-dried pranlukast granules. The resulting granules had an average particle size of about 10 μm.

Spray-drying Conditions:
  Disk rotational speed: 25000 rpm
  Air temperature at the inlet: 185° C.
  Air temperature at the outlet: 95° C.

COMPARATIVE EXAMPLE 1

In a agitation granulator were put 10 kg of pranlukast and 5 kg of lactose, and a solution of 1 kg of polyethylene glycol in 2 kg of purified water was added thereto, followed by kneading. The blend was extruded through an extrusion granulator into granules, dried in a fluidized bed drier, and classified to obtain pranlukast granules.

COMPARATIVE EXAMPLE 2

In a high-speed agitation granulator were put 10 kg of pranlukast and 5 kg of lactose, and a solution of 1 kg of polyethylene glycol in 2 kg of purified water was added thereto. The mixture was granulated, dried in a fluidized bed drier, and classified to obtain pranlukast granules.

TEST EXAMPLE 1

Attention being given to the fact that stickiness is lessened as the amount of magnesium stearate added as a lubricant increases, the suitability for capsule-filling was evaluated with magnesium stearate added in a varied amount. Specifically, the granules obtained in Example 4 or Comparative Examples 1 or 2 were mixed with magnesium stearate added in an amount of 1, 2, 4 or 6 wt % and charged into capsules. The results obtained are shown in Table 1 below.

TABLE 1

| Amount added | 1% | 2% | 4% | 6% |
| --- | --- | --- | --- | --- |
| Example 4 | ± | − | | |
| Comparative Example 1 | ++ | + | ± | − |
| Comparative Example 2 | ++ | ++ | + | ± |

++: The granules were so sticky that capsule-filling was difficult.
+: The granules tended to be sticky, and continuous capsule-filling was impossible.
±: The granules tended to be slightly sticky, and continuous capsule-filling was slightly difficult.
−: The granules were not sticky and could be continuously capsule-filled.

The amount of magnesium stearate being taken as a measure of suitability in capsule-filling, the results of Table 1 show that the stickiness of the spray-dried granules of Example 4 to the turn table and the like is reduced to one-third or less of that of the extruded granules of Comparative Example 1 and the granules of Comparative Example 2 obtained by high-speed agitation granulation.

TEST EXAMPLE 2

The powder properties of pranlukast raw powder and the granules obtained in Example 4 and Comparative Example 2 were evaluated with a powder bed tester (an instrument for measuring dynamic physical properties of a powder layer). The results obtained are shown in Table 2.

TABLE 2

| Sample | Shear adhesive strength | Tensile strength at break | Monoaxial compressive strength |
| --- | --- | --- | --- |
| Pranlukast powder | 8.78 | 4.27 | 34.69 |
| Comparative Example 2 | 1.65 | 0.74 | 8.83 |
| Comparative Example 4 | 0.52 | 0.17 | 2.96 |

(unit: $g/cm^2$)

The data of physical properties in Table 2 provide confirmation that pranlukast is very strongly adhesive powder. Notwithstanding the fact that the pranlukast granules of Example 4 and Comparative Example 2 have the same composition, the adhesiveness of the former (the present invention) shows reduction to about ⅓ to ¼ of that of the latter (prepared by conventional high-speed agitation granulation). That is, the results of Test Example 1 are supported by the physical data.

INDUSTRIAL APPLICABILITY

According to the present invention pranlukast-containing granules having little adhesiveness, a narrow particle size distribution, and very good flow properties can be produced efficiently.

The pranlukast-containing granules of the present invention are advantageous in that no troubles occur in continuous production of capsules, tablets, etc. and the granules exhibit excellent disintegrating and dispersing properties.

What is claimed is:

1. Spray-dried granules comprising pranlukast (A) and one or more saccharide(s) (B) as essential ingredients and further comprising one or more water-soluble polymer(s) (C) and/or one or more surfactant(s) (D).

2. The spray-dried granules according to claim 1, which comprise one or more saccharide(s) (B) and one or more water-soluble polymer(s) (C).

3. The spray-dried granules according to claim 1, which comprise one or more saccharide(s) (B) and one or more surfactant(s) (D).

4. The spray-dried granules according to claim 1, which comprise one or more saccharide(s) (B), one or more water-soluble polymer(s) (C), and one or more surfactant(s) (D).

5. The spray-dried granules according to any one of claims 1 to 4, wherein the saccharide is lactose or mannitol.

6. The spray-dried granules according to claim 1, wherein the water-soluble polymer (C) is a cellulose compound or a synthetic polymer.

7. The spray-dried granules according to claim 2, wherein the water-soluble polymer (C) is a cellulose compound or a synthetic polymer.

8. The spray-dried granules according to claim 4, wherein the water-soluble polymer (C) is a cellulose compound or a synthetic polymer.

9. The spray-dried granules according to claim 6, wherein the water-soluble polymer (C) is hydroxypropyl cellulose, polyvinylpyrrolidone or polyethylene glycol.

10. The spray-dried granules according to claim 7, wherein the water-soluble polymer (C) is hydroxypropyl cellulose, polyvinylpyrrolidone or polyethylene glycol.

11. The spray-dried granules according to claim 8, wherein the water-soluble polymer (C) is hydroxypropyl cellulose, polyvinylpyrrolidone or polyethylene glycol.

12. The spray-dried granules according to claim 1, wherein the surfactant (D) is polysorbate.

13. The spray-dried granules according to claim 3, wherein the surfactant (D) is polysorbate.

14. The spray-dried granules according to claim 4, wherein the surfactant (D) is polysorbate.

15. The spray-dried granules according to claim 1, which comprise pranlukast (A); lactose and/or mannitol (B1); hydroxypropyl cellulose, polyvinylpyrrolidone, polyethylene glycol (C1) and/or polysorbate; and which further contain or do not contain ammonium carbonate (E1).

16. The spray-dried granules according to claim 15, comprise pranlukast (A), lactose (B2), and hydroxypropyl cellulose (C2).

17. The spray-dried granules according to claim 15, comprise pranlukast (A), lactose (B2), and polyethylene glycol (C3).

18. A process for producing spray-dried granules comprising spray-drying a suspension comprising pranlukast (A) and one or more saccharide(s) (B) as essential ingredients and further comprising one or more water-soluble polymer (s) (c) and/or one or more surfactant(s) (D).

19. A method of improving adhesiveness of pranlukast comprising spray-drying into granules a suspension comprising pranlukast (A) and one or more saccharide(s) (B) as essential ingredients and further comprising one or more water-soluble polymer(s) (C) and/or one or more surfactant (s) (D).

* * * * *